United States Patent
Hsia et al.

(10) Patent No.: US 12,371,705 B2
(45) Date of Patent: Jul. 29, 2025

(54) INDUCIBLE PROMOTER FOR RICE EXPRESSION SYSTEM, SYNTHETIC BIOLOGICAL PLATFORM AND USE THEREOF

(71) Applicant: GUANGDONG COOPERATE BIOTECHNOLOGY CO., LTD., Guangdong (CN)

(72) Inventors: Chun Chi Hsia, Guangdong (CN); Zhong Liu, Guangdong (CN); Man Mei Li, Guangdong (CN); Chia Wen Li, Guangdong (CN); Pi Hung Liao, Guangdong (CN); Yu Chun Wu, Guangdong (CN)

(73) Assignee: GUANGDONG COOPERATE BIOTECHNOLOGY CO., LTD., Zhongshan (CN)

( * ) Notice: Subject to any disclaimer, the term of this patent is extended or adjusted under 35 U.S.C. 154(b) by 0 days.

(21) Appl. No.: 18/604,547

(22) Filed: Mar. 14, 2024

(65) Prior Publication Data

US 2024/0218388 A1 Jul. 4, 2024

Related U.S. Application Data

(63) Continuation of application No. PCT/CN2021/132881, filed on Nov. 24, 2021.

(30) Foreign Application Priority Data

Sep. 14, 2021 (CN) .......................... 202111073635.0

(51) Int. Cl.
C12N 15/82 (2006.01)
A61K 8/9794 (2017.01)
A61Q 19/00 (2006.01)

(52) U.S. Cl.
CPC ........ *C12N 15/8257* (2013.01); *A61K 8/9794* (2017.08); *A61Q 19/007* (2013.01); *C12N 15/8222* (2013.01)

(58) Field of Classification Search
CPC ............ C12N 15/8257; C12N 15/8222; A61K 8/9794; A61Q 19/007
See application file for complete search history.

(56) References Cited

U.S. PATENT DOCUMENTS 7,365,185 B2 * 4/2008 Boukharov ........ C12N 15/8216 536/24.1
2011/0047648 A1 2/2011 Kim et al.
2013/0074219 A1 3/2013 Kim et al.

FOREIGN PATENT DOCUMENTS

| CN | 103732758 A | 4/2014 |
|----|-------------|--------|
| CN | 105263965 A | 1/2016 |
| CN | 107267508 A | 10/2017 |
| JP | 2005022993 A | 1/2005 |
| TW | 202102528 A | 1/2021 |
| WO | 2010067914 A1 | 6/2010 |
| WO | WO-2021170839 A1 * | 9/2021 ............. C07K 14/78 |

OTHER PUBLICATIONS

Llaca,V., Lou,A., Young,S., Kavchok,S. and Messing,J. *Oryza sativa* subsp. *japonica* BAC clone nbxb0032120, complete sequence. Genbank Accession No. AF229187.1 (2000) (Year: 2000).*
The Rice Chromosome 10 Sequencing Consortium. "In-Depth view of structure, activity, and evolution of Rice Chromosome 10". Science, vol. 300 (Jun. 6, 2003), pp. 1566-1569 (Year: 2003).*
UCSC Genome browser-pdf-1-retrieved from internet Jun. 29, 2024. (Year: 2024).*
UCSC Genome browser-pdf-2-retrieved from internet Jun. 29, 2024. (Year: 2024).*
Beaudoin, N. and Rothstein, S. "Developmental regulation of two tomato lipoxygenase promoters in transgenic tobacco and tomato." Plant Molecular Biology, vol. 33 (1997), pp. 835-846. (Year: 1997).*
Memelink, J. "Regulation of gene expression by jasmonate hormones". Phytochemistry, vol. 70 (2009), pp. 1560-1570. (Year: 2009).*
Jing Yang et al., Elastin-like polypeptide and γ-zein fusions significantly increase recombinant protein accumulation in soybean seeds, Transgenic Research, May 8, 2021.
V. Llaca et al., *Oryza sativa* subsp. *japonica* BAC clone nbxb0032120, complete sequence, Sequence ID: AF229187.1, NCBI.
D.Y. Li et al., Elastin, pertial [*Homo sapiens*], GenBank: AAB65620. 1, 602aa linear, NCBI.
Tiantian Li et al., Cloning and Functional Identification of MeJA and Bacterial Blight-induced Promoter in Rice, Molecular Plant Breeding, 2018, pp. 689-695, vol. 16, No. 3.
Ang Li et al., Analysis of the essential DNA region for OsEBP-89 promoter in response to methyl jasmonic acid, Science in China Series C: Life Sciences, Mar. 2008, pp. 280-285, vol. 51, No. 3.
J. Sambrook et al., Molecular Cloning, 1989.
Jan A Witkowski, Cold Spring Harbor Laboratory, pp. 1-5.
Mansour Karimi et al., Gateway™ vectors for Agrobacterium-mediated plant transformation, Trends in Plant Science, May 2002, pp. 193-195, vol. 7, No. 5.
Asuka Nishimura et al., A protocol for Agrobacterium-mediated transformation in rice, Nature Protocols, 2006, pp. 2796-2802, vol. 1, No. 6.

(Continued)

*Primary Examiner* — Anna Skibinsky
*Assistant Examiner* — Alexandra Geraldine Dace Denito (57) ABSTRACT

Provided is a promoter sequence induced by methyl jasmonate. Also provided are an expression cassette, a recombinant vector and a recombinant cell comprising the promoter sequence. In addition, further provided is a method for producing an exogenous protein using the expression vector, and in particular a method for producing a human elastin in a rice cell using the expression vector. Further provided is a skin care composition comprising the exogenous protein. The composition is not cytotoxic to HaCaT cell lines and CCD966SK cell lines, and can increase the expression levels of water retention-related genes hHAS2, hHAS3, hAQP3 and hFLG in a cell, thereby improving the water retention and barrier functions in the cell as well as having a broad application prospect.

12 Claims, 6 Drawing Sheets

Specification includes a Sequence Listing.

(56) References Cited

OTHER PUBLICATIONS

Chung-An Lu et al., Sugar Response Sequence in the Promoter of a Rice a-Amylase Gene Serves as a Transcriptional Enhancer, The Journal of Biological Chemistry, Apr. 24, 1998, pp. 10120-10131, vol. 273, No. 17.
Notice of Allowance of counterpart Chinese Patent Application No. 202111073635.0 issued on Jul. 7, 2023.
First Search Report of counterpart Chinese Patent Application No. 202111073635.0 issued on Jul. 5, 2023.

\* cited by examiner

A pMeJA-GFP-GUS

B pCAM-OsMeJA-hPELN-Ostml

```
                        SEQUENCE LISTING

Sequence total quantity: 25
SEQ ID NO: 1            moltype = DNA  length = 36
FEATURE                 Location/Qualifiers
source                  1..36
                        mol_type = other DNA
                        organism = synthetic construct
SEQUENCE: 1
aaaaagcagg cttcctttcc aacatatcgg tatctc                             36

SEQ ID NO: 2            moltype = DNA  length = 32
FEATURE                 Location/Qualifiers
source                  1..32
                        mol_type = other DNA
                        organism = synthetic construct
SEQUENCE: 2
agaaagctgg gttggtgact tctgtgatgg ag                                 32

SEQ ID NO: 3            moltype = DNA  length = 1034
FEATURE                 Location/Qualifiers
source                  1..1034
                        mol_type = other DNA
                        organism = Oryza sativa
SEQUENCE: 3
ttggcttatg atgacaacta cgacactaca aatcaatttt cacaatgaat ctgctcttaa   60
tttagtgaga gcaaccatga ggacgatgct tcacaggcaa gtgctattgc tctgctagcc  120
tgctacatgc agttccaatt aatgtgtatc tcaaaccttt acagaacatg tattatttat  180
gagaaaaaga tgtccgcata tcctttccaa catatcggta tctcatcttt ttaagtcaaa  240
attgttagta tcagaacaga atatctatca gatagcaggc ctaactttct gacctactcc  300
ttatatctta gttcagggtt gttcacagaa gaaacagccc aatttagcag ctgttctttc  360
cttttctcct gtcactgtag caagagagaa agaaagtgaa agattagccc cactattcac  420
aaactactga aatagatcca agaagaaaag tatttcaaaa agaaaatttg aaaaagaata  480
atgtttttttt tctcctgtca gtcatgccaa aatccaaatg agacagtgta gttgacctttt 540
gcagtcaacc agtttggcct ctgtactagc cctgctttgg atcttctgga agctgtccct  600
gtaaggttta cttcagtttg tggatttcaa aagttgggac ttttctttga tatagttagt  660
tggaagagta agacagaagt gtacctaata atcagaaaat tgtgaatttt tttagtcaca  720
tattctctct tcacatctta aagattatcc tgcatggcaa atcaaataag agtcagccat  780
tgaggaaccc ttccaacctc atccaatcga atcagttgaa aattttgacc ttatctccta  840
cattcaaacc ttggttgagc agtccattca gaaggctctg tttcttcagc accatttaat  900
ttttcatttg acaaaatctt ggtggttgat ttgtgagcca caaacaagt tataaattca   960
gcgttcttct gaagattgca gcagcgtcct caaccaatca attgcaagca atttctccat 1020
cacagaagtc acca                                                   1034

SEQ ID NO: 4            moltype = DNA  length = 32
FEATURE                 Location/Qualifiers
source                  1..32
                        mol_type = other DNA
                        organism = synthetic construct
SEQUENCE: 4
ccaagctttc ctttccaaca tatcggtatc tc                                 32

SEQ ID NO: 5            moltype = DNA  length = 29
FEATURE                 Location/Qualifiers
source                  1..29
                        mol_type = other DNA
                        organism = synthetic construct
SEQUENCE: 5
aaccatggcg aggttggagt ttactgccg                                     29

SEQ ID NO: 6            moltype = DNA  length = 75
FEATURE                 Location/Qualifiers
```

```
                    source          1..75
                                    mol_type = other DNA
                                    organism = Oryza sativa
SEQUENCE: 6
atgggctccg ccaagctcat tgctgtagtc ctcctcccgg cccttctggc cttccaagct    60
ccaatggcca cggca                                                     75

SEQ ID NO: 7        moltype = DNA   length = 30
FEATURE             Location/Qualifiers
source              1..30
                    mol_type = other DNA
                    organism = synthetic construct
SEQUENCE: 7
aaccatggtc ccactggggt atcccatcaa                                     30

SEQ ID NO: 8        moltype = DNA   length = 31
FEATURE             Location/Qualifiers
source              1..31
                    mol_type = other DNA
                    organism = synthetic construct
SEQUENCE: 8
ccagatcttc aaatgcctcc aactccgact c                                   31

SEQ ID NO: 9        moltype = DNA   length = 585
FEATURE             Location/Qualifiers
source              1..585
                    mol_type = other DNA
                    organism = Homo sapiens
SEQUENCE: 9
atggtcccac tggggtatcc catcaaggcc cccaagctgc ctggtggcta tggactgccc    60
tacaccacag ggaaactgcc ctatggctat gggcccggag gagtggctgg tgcagcgggc   120
aaggctggtt acccaacagg gacaggggtt ggccccagg cagcagcagc agcggcagct    180
aaagcagcag caaagttcgg tgctggagca gccggagtcc tccctggtgt tggaggggct   240
ggtgttcctg gcgtgcctgg ggcaattcct ggaattggag gcatcgcagg cgttgggact   300
ccagctgcag ctgcagctgc agcagcagcc gctaaggcag ccaagtatgg tgctgctgca   360
ggcttagtgc ctggtgggcc aggctttggc ccgggagtag ttggtgtccc aggagctggc   420
gttccaggtg ttggtgtccc aggagctggg attccagttg tcccaggtgc tgggatccca   480
ggtgctgcgg ttcaggggt tgtgtcacca gaagcagctg ctaaggcagc tgcaaaggca    540
gccaaatacg gggccaggcc cggagtcgga gttggaggca tttga                   585

SEQ ID NO: 10       moltype = DNA   length = 40
FEATURE             Location/Qualifiers
source              1..40
                    mol_type = other DNA
                    organism = synthetic construct
SEQUENCE: 10
gagaaaatga agatctataa atctagcata tacataggct                          40

SEQ ID NO: 11       moltype = DNA   length = 42
FEATURE             Location/Qualifiers
source              1..42
                    mol_type = other DNA
                    organism = synthetic construct
SEQUENCE: 11
tggtcacctg taattcacac gtggtacaac atgcccaata ca                       42

SEQ ID NO: 12       moltype = DNA   length = 263
FEATURE             Location/Qualifiers
source              1..263
                    mol_type = other DNA
                    organism = synthetic construct
SEQUENCE: 12
ataaatctag catatacata ggctatgcgt acaatacgat aatgcataca tacatacgtc    60
gtaccgtgta gcagtatatg cagatgtgag atcaatccca ataatagtat ttatgtttat   120
gtttaatttc aggaatatgt atgcaacgaa taaatcatat gtaaaaggtt atatatgtat   180
aaagttgtat caccttatt tatcatgcta gctgcagttt gtttggaata aattaataaa    240
gatgtgtatt gggcatgttg tac                                           263

SEQ ID NO: 13       moltype = DNA   length = 20
FEATURE             Location/Qualifiers
source              1..20
                    mol_type = other DNA
                    organism = synthetic construct
SEQUENCE: 13
cctcatcatc caaagcctgt                                                20

SEQ ID NO: 14       moltype = DNA   length = 20
FEATURE             Location/Qualifiers
source              1..20
```

```
                            mol_type = other DNA
                            organism = synthetic construct
SEQUENCE: 14
aaacagttgc cctttgcatc                                                      20

SEQ ID NO: 15               moltype = DNA   length = 20
FEATURE                     Location/Qualifiers
source                      1..20
                            mol_type = other DNA
                            organism = synthetic construct
SEQUENCE: 15
gtcatgtaca cggccttcaa                                                      20

SEQ ID NO: 16               moltype = DNA   length = 20
FEATURE                     Location/Qualifiers
source                      1..20
                            mol_type = other DNA
                            organism = synthetic construct
SEQUENCE: 16
cctacttggg gatcctcctc                                                      20

SEQ ID NO: 17               moltype = DNA   length = 20
FEATURE                     Location/Qualifiers
source                      1..20
                            mol_type = other DNA
                            organism = synthetic construct
SEQUENCE: 17
catctacacc ctggcacaga                                                      20

SEQ ID NO: 18               moltype = DNA   length = 20
FEATURE                     Location/Qualifiers
source                      1..20
                            mol_type = other DNA
                            organism = synthetic construct
SEQUENCE: 18
ggctgtgcct atgaactggt                                                      20

SEQ ID NO: 19               moltype = DNA   length = 26
FEATURE                     Location/Qualifiers
source                      1..26
                            mol_type = other DNA
                            organism = synthetic construct
SEQUENCE: 19
gttacaattc caatcctgtt gttttc                                               26

SEQ ID NO: 20               moltype = DNA   length = 24
FEATURE                     Location/Qualifiers
source                      1..24
                            mol_type = other DNA
                            organism = synthetic construct
SEQUENCE: 20
cgttgcataa taccttggat gatc                                                 24

SEQ ID NO: 21               moltype = DNA   length = 100
FEATURE                     Location/Qualifiers
source                      1..100
                            mol_type = other DNA
                            organism = Homo sapiens
SEQUENCE: 21
cctcatcatc caaagcctgt ttgccttttt ggagcaccga aaaatgaaaa aatccctaga          60
aaccccccata aagttgaaca aaacagttgc cctttgcatc                              100

SEQ ID NO: 22               moltype = DNA   length = 131
FEATURE                     Location/Qualifiers
source                      1..131
                            mol_type = other DNA
                            organism = Homo sapiens
SEQUENCE: 22
gtcatgtaca cggccttcaa ggccctcggc gattcggtgg actacatcca ggtgtgcgac          60
tctgacactg tgctggatcc agcctgcacc atcgagatgc ttcgagtcct ggaggaggat         120
ccccaagtag g                                                             131

SEQ ID NO: 23               moltype = DNA   length = 202
FEATURE                     Location/Qualifiers
source                      1..202
                            mol_type = other DNA
                            organism = Homo sapiens
SEQUENCE: 23
catctacacc ctggcacaga cgctgggagc cttcttgggt gctggaatag ttttgggct           60
```

```
gtattatgat gcaatctggc acttcgccga caaccagctt tttgtttcgg gccccaatgg    120
cacagccggc atctttgcta cctaccnctc tggacacttg gatatgatca atggcttctt    180
tgaccagttc ataggcacag cc                                             202

SEQ ID NO: 24           moltype = DNA  length = 92
FEATURE                 Location/Qualifiers
source                  1..92
                        mol_type = other DNA
                        organism = Homo sapiens
SEQUENCE: 24
gttacaattc caatcctgtt gttttcaagg aaagatctga tatctgtaaa gcaagtgcgt    60
ttggtaaaga tcatccaagg tattatgcaa cg                                  92

SEQ ID NO: 25           moltype = AA   length = 194
FEATURE                 Location/Qualifiers
source                  1..194
                        mol_type = protein
                        organism = Homo sapiens
SEQUENCE: 25
MVPLGYPIKA PKLPGGYGLP YTTGKLPYGY GPGGVAGAAG KAGYPTGTGV GPQAAAAAAA    60
KAAAKFGAGA AGVLPGVGGA GVPGVPGAIP GIGGIAGVGT PAAAAAAAAA AKAAKYGAAA   120
GLVPGGPGFG PGVVGVPGAG VPGVGVPGAG IPVVPGAGIP GAAVPGVVSP EAAAKAAAKA   180
AKYGARPGVG VGGI                                                     194
```

INDUCIBLE PROMOTER FOR RICE EXPRESSION SYSTEM, SYNTHETIC BIOLOGICAL PLATFORM AND USE THEREOF

CROSS-REFERENCE TO RELATED APPLICATIONS

The present application is a continuation application of PCT application No. PCT/CN2021/132881 filed on Nov. 24, 2021, which claims the benefit of Chinese Patent Application No. 202111073635.0 filed on Sep. 14, 2021. The contents of all of the aforementioned applications are incorporated by reference herein in their entirety.

REFERENCE TO SEQUENCE LISTING

This application includes a Sequence Listing filed electronically as a text file named Sequence listing_RONDA-24004-USPT.xml, created on Mar. 13, 2024, with a size of 25,745 bytes. The Sequence Listing is incorporated herein by reference.

TECHNICAL FIELD

The present disclosure relates to the field of plant molecular biology and, more specifically, to an inducible promoter for a rice expression system, a synthetic biological platform and use thereof.

BACKGROUND

Currently, molecular farming is widely used to produce exogenous proteins such as enzymes, antibodies, and pharmaceutical proteins. Commercially available molecular farming expression systems include bacterial expression systems, yeast expression systems, fungal expression systems, mammalian expression systems, plant expression systems, insect expression systems, and the like.

The lack of post-translational modifications in bacterial expression systems results in the protein products that are less biologically active and are often produced in the form of inclusion bodies, making protein purification difficult. In addition, bacterial expression systems suffer from the safety issue of incomplete endotoxin removal during protein purification.

Although mammalian expression systems have post-translational modification capabilities, mammalian expression systems suffer from application issues such as low protein yields, high production costs, complex operating procedures and risk of contamination during the production of exogenous proteins.

Plant expression systems have a number of advantages over other expression systems, including smaller capital requirements, lower production and cultivation costs, higher yields, and the post-translational modification capabilities of the exogenous proteins as produced in the plant, so that the exogenous proteins have functions and activities close to those of the original proteins.

Elastin, which forms elastic fibers, is a protein that maintains the elasticity of connective tissues in vertebrates and allows many tissues in vertebrates to return to their original shape after stretching or contracting. In addition, elastin has a high economic value and can be widely used in pharmaceutical and cosmetic uses. For example, it can be used as a support material for stem cell culture systems to enable the growth of stem cells, as a filler ingredient for hypodermic injections, as a surgical wound healing gel, as a material for 3D printing, and as an additive for moisturizing and anti-aging cosmetics or oral nutritional supplements, and the like.

Currently, elastin is mainly extracted from animal tissues. In the prior art, elastin is extracted from the aorta tissues of animals. However, due to the large degree of variation in the amino acid sequences of elastin between species, for example, the similarity between human elastin and porcine elastin is only 79%, and the similarity between human elastin and bovine elastin is only 78%, elastin extracted from animal tissues may cause an allergic reaction in the human body, and there may also be a risk of zoonotic infection.

Therefore, the development of low-cost and high-yield expression systems that produce exogenous proteins with functions and activities close to those of the original proteins is a pressing problem in the art.

SUMMARY

It is an object of the present disclosure to provide an isolated promoter sequence, an expression vector comprising the isolated promoter sequence, a transgenic plant cell comprising the expression vector, a method for expressing a target gene, and a skin care composition.

The technical solutions as used in the present disclosure are as follows:

In a first aspect according to the present disclosure, there is provided a nucleic acid molecule selected from any one of the following (I) to (III):
  (I) a nucleic acid molecule having a nucleotide sequence as set forth in SEQ ID NO: 3;
  (II) a nucleic acid molecule having 90% or more identity to the nucleotide sequence defined in (I) and having a promoter function; and
  (III) a nucleic acid molecule hybridizing to the nucleotide sequence defined in (I) and having a promoter function.

Those of ordinary skill in the art can readily mutate the nucleotide sequences of the specific DNA molecules according to the present disclosure using known methods, such as directed evolution and point mutation. Those nucleotides that have been artificially modified to have 75% or greater identity to the nucleotide sequences of the nucleic acid molecules provided herein are derived from and are equivalent to the nucleotide sequences according to the present disclosure as long as they have promoter function.

The term "identity" as used herein refers to sequence similarity to a natural nucleic acid sequence. "Identity" includes nucleotide sequences having 75% or greater, 80% or greater, or 85% or greater, or 90% or greater, or 95% or greater identity to the nucleotide sequence of the nucleic acid molecule according to the present disclosure. The identity may be evaluated by the naked eye or by computer software. The identity between two or more sequences can be expressed as a percentage (%) using computer software, which can be used to evaluate the identity between related sequences.

In a second aspect according to the present disclosure, there is provided an expression cassette comprising the nucleic acid molecule as described in the first aspect according to the present disclosure.

Further, said expression cassette may comprise a promoter region consisting of the nucleic acid molecule as described in the first aspect according to the present disclosure, a transcription initiation region, a target gene region, a transcription termination region and optionally a translation termination region from the 5' end to the 3' end. Said promoter region and target gene region may be natural/similar to the host cell, or said promoter region and target gene region may be natural/similar to each other, or said promoter region and/or target gene region may be heterologous to the host or to each other. "Heterologous" means that the sequence is of exotic origin or, if of the same species, that the natural form has been substantially modified in terms of components and/or genomic loci by deliberate human intervention. The optionally transcription termination region may be homologous to the transcription initiation region, homologous to the operably linked target gene region, homologous to the host; or exogenous or heterologous to the target gene region and the host.

Said expression cassette may also comprise a guide sequence at the 5' end. The guide sequence at the 5' end can enhance translation.

In preparing expression cassettes, adapters or linkers may be applied to join DNA fragments, or other manipulations can be used to provide appropriate restriction sites, remove excess DNA, remove restriction sites, and the like. In vitro mutation, primer repair, restriction enzyme cleavage, annealing, and re-substitution, such as conversion and inversion, may be performed for this purpose.

Said expression cassette may further comprise a selective marker gene for screening transformed cells. The selective marker genes may be used to screen transformed cells or tissues. Marker genes include genes encoding antibiotic resistance. Other selective markers include phenotypic markers such as GUS proteins and fluorescent proteins. The selective markers as listed above are not limiting. Any selective marker gene may be used in the present disclosure.

In a third aspect according to the present disclosure, there is provided a vector comprising the nucleic acid molecule as described in the first aspect according to the present disclosure. Further, said vector further contains a target gene sequence.

Still further, said target gene may be codon optimized. Those of ordinary skill in the art can readily employ known methods for codon optimization of a target gene sequence based on the transcriptional and translational preferences of a host cell.

Still further, said target gene is a nucleotide sequence of human elastin or a nucleotide sequence of partial human elastin.

Said partial human elastin is more preferably a partial fragment of a sequence conserved region in a plurality of human elastin with modified mRNA (RNA splicing).

Preferably, the amino acid sequence of said partial human elastin is as set forth in SEQ ID NO: 25.

More preferably, the nucleotide sequence of said partial human elastin is as set forth in SEQ ID NO: 9.

Still further, said vector further contains a transcription initiation sequence, a target gene sequence, a transcription termination sequence, and optionally a translation termination sequence.

Still further, said vector may also comprise a guide sequence at the 5' end. The guide sequence at the 5' end can enhance translation.

Still further, said vector may also include adapters or linkers that may be applied to join DNA fragments, or other manipulations that can be used to provide appropriate restriction sites, remove excess DNA, remove restriction sites, and the like.

Still further, said vector may also comprise a selective marker gene for screening transformed cells. The selective marker genes may be used to screen transformed cells or tissues. Marker genes include genes encoding antibiotic resistance. Other selective markers include phenotypic markers such as GUS proteins and fluorescent proteins. The selective markers as listed above are not limiting. Any selective marker gene may be used in the present disclosure.

More specifically, said vector comprises a nucleotide sequence of hygromycin phosphotransferase (hpt).

More specifically, said vector comprises a nucleotide sequence of a signal peptide (SP).

Preferably, the nucleotide sequence of said signal peptide is as set forth in SEQ ID NO: 6.

More specifically, said vector comprises a terminator sequence.

More specifically, said vector comprises, among other things, a nucleotide sequence of a kanamycin resistance gene.

More preferably, the nucleic acid molecule as described in the first aspect according to the present disclosure is located upstream of said target gene sequence.

More preferably, said signal peptide sequence is located between the nucleic acid molecule as described in the first aspect according to the present disclosure and the target gene sequence.

More preferably, said terminator sequence is located downstream of said target gene sequence.

In a fourth aspect according to the present disclosure, there is provided a cell comprising a vector as described in the third aspect according to the present disclosure. Said cell is a new species of a non-plant or animal.

Preferably, said cells are *Agrobacterium* cells.

Preferably, said cells are rice cells, *Arabidopsis thaliana* cells, tobacco cells, carrot cells or tomato cells.

More preferably, said cells are rice suspension cells, *Arabidopsis thaliana* suspension cells, tobacco suspension cells, carrot suspension cells or tomato suspension cells as obtained based on plant suspension culture techniques.

In a fifth aspect according to the present disclosure, there is provided use of the nucleic acid molecule as described in the first aspect according to the present disclosure as a promoter.

Further, said promoter is induced by methyl jasmonate.

In a sixth aspect according to the present disclosure, there is provided use of the nucleic acid molecule as described in the first aspect according to the present disclosure, the expression cassette as described in the second aspect according to the present disclosure, the vector as described in the third aspect according to the present disclosure, or the cell as described in the fourth aspect according to the present disclosure in the initiation of the expression of a target gene.

In a seventh aspect according to the present disclosure, there is provided a method for expressing a target gene using the nucleic acid molecule as described in the first aspect according to the present disclosure as a promoter to initiate the expression of the target gene.

In an eighth aspect according to the present disclosure, there is provided a method for expressing a target gene, comprising the steps as described in any one of the following (I) to (III):
  (I) inserting the nucleic acid molecule as described in the first aspect according to the present disclosure upstream of any target gene or enhancer;
  (II) inserting the target gene downstream of said nucleic acid molecule of the expression cassette as described in the second aspect according to the present disclosure; and
  (III) inserting the target gene downstream of said nucleic acid molecule of the vector as described in the third aspect according to the present disclosure.

In a ninth aspect according to the present disclosure, there is provided a method for constructing a transgenic plant, comprising the step of transferring the nucleic acid molecule as described in the first aspect according to the present disclosure, the expression cassette as described in the second aspect according to the present disclosure, or the vector as described in the third aspect according to the present disclosure into a recipient plant.

Preferably, said plant is rice, *Arabidopsis thaliana*, tobacco, carrot or tomato.

In a tenth aspect according to the present disclosure, there is provided a composition comprising any one of the following (I) to (III):
(I) an expression product of a target gene obtained by the method as described in the seventh aspect according to the present disclosure;
(II) an expression product of a target gene obtained by the method as described in the eighth aspect according to the present disclosure; and
(III) a culture, isolate or extract of a transgenic plant constructed by the method as described in the ninth aspect according to the present disclosure.

Preferably, said expression product of the target gene includes a cell culture, isolate or extract. More preferably, the transgenic plant culture or the transgenic plant cell culture is filtered to obtain a filtrate; the filtrate is dialyzed to obtain a dialysate; and the dialysate is filtered to obtain a plant extract.

Preferably, said target gene is a nucleotide sequence of human elastin or a nucleotide sequence of partial human elastin.

More preferably, the nucleotide sequence of said partial human elastin is as set forth in SEQ ID NO: 9.

Preferably, said transgenic plant is rice, *Arabidopsis thaliana*, tobacco, carrot or tomato.

More preferably, said transgenic plant extract is obtained by filtering the transgenic plant culture to obtain a filtrate; dialyzing the filtrate to obtain a dialysate; and filtering the dialysate to obtain a plant extract.

In an eleventh aspect according to the present disclosure, there is provided use of the composition as described in the tenth aspect according to the present disclosure in the manufacture of a cosmetic or skin care product.

Further, said cosmetic or skin care product has the function of moisturizing the skin and/or repairing the skin barrier.

The beneficial effects according to the present disclosure are as follows:

The present disclosure provides a promoter sequence induced by methyl jasmonate. An expression cassette, a recombinant vector, and a recombinant cell comprising the promoter sequence are also provided. Also provided is a method for producing an exogenous protein using the expression vector; in particular, a method for producing human elastin in a rice cell using the expression vector. Also, the present disclosure provides a skin care composition comprising the above exogenous protein. The composition is not cytotoxic to HaCaT cell lines and CCD966SK cell lines, and can increase the gene expression levels of hHAS2 and hHAS3, human hyaluronan synthases related to water retention, by 9% and 15%, respectively, hAQP3, human aquaporin related to cell permeability, by 15%, and hFLG, human filaggrin related to cellular structure and barrier function, by 9% in the CCD966SK cell lines. The increase in cellular gene expression levels of hHAS2, hHAS3, hAQP3, and hFLG can enhance cellular water retention and barrier function.

BRIEF DESCRIPTION OF FIGURES

FIG. 1 is a graph showing a schematic structure of the plasmid. A of FIG. 1 is a graph showing a pMeJA-GFP-GUS plasmid, where OsMeJA promoter represents a promoter sequence from rice that can be induced by methyl jasmonate; GFP-GUS represents a green fluorescent protein-β-glucuronidase reporter gene; and NOS represents a terminator sequence. B of FIG. 1 is a graph showing a pCAM-OsMeJA-hPELN-Ostml plasmid, where LB represents a left border sequence embedded in DNA; RB represents a right border sequence embedded in DNA; hpt represents a nucleotide sequence of hygromycin phosphotransferase (hpt); OsMeJA represents a promoter sequence from *Oryza sativa* L. cv Tainung 67 that can be induced by methyl jasmonate; SP represents a nucleotide sequence of signal peptide (SP); hPELN represents a nucleotide sequence of partial human elastin; Ostml represents a terminator sequence from rice; NOS represents a terminator sequence; and KanR represents a nucleotide sequence of the kanamycin resistance gene.

DETAILED DESCRIPTION

The conception according to the present disclosure and the resulting technical effects will be described clearly and completely in connection with the following examples, so as to fully understand the purpose, features and effects according to the present disclosure. Obviously, the examples described are only a portion of the examples according to the present disclosure, and not all of them. Based on the examples according to the present disclosure, other examples obtained by those skilled in the art without creative labor are within the protection scope according to the present disclosure.

Experimental methods for which specific conditions are not noted in the following examples are generally performed under routine conditions, such as those described in Sambrook et al, Molecular Cloning: A Laboratory Manual (New York: Cold Spring Harbor Laboratory Press, 1989), or under conditions recommended by the manufacturer. Various common chemical reagents used in the examples are commercially available.

Example 1 Construction of pMeJA-GFP-GUS Plasmid

The leaf genomic DNA of *Oryza sativa* L. cv Tainung 67 was extracted. A first primer pair comprising a forward primer having the sequence as set forth in SEQ ID NO: 1 and a reverse primer having the sequence as set forth in SEQ ID NO: 2 was designed and a polymerase chain reaction (PCR) was performed using the rice genomic DNA as the template DNA for PCR to amplify a full-length nucleotide sequence of OsMeJA promoter as set forth in SEQ ID NO: 3. Subsequently, the full-length nucleotide sequence of OsMeJA promoter was embedded into a pHGWFS7 target vector with a green fluorescent protein-β-glucuronidase (GFP-GUS) reporter gene (Thermo Fisher Scientific, Massachusetts, USA) using Gateway® technology according to Karimi et al. (2002) to obtain the pMeJA-GFP-GUS plasmid as shown in A of FIG. 1.

Example 2 Construction of pCAM-OsMeJA-SP-hPELN-Ostml Plasmid

A second primer pair comprising a forward primer having the sequence as set forth in SEQ ID NO: 4 and a reverse primer having the sequence as set forth in SEQ ID NO: 5 was designed, and a PCR was performed using the rice genomic DNA as the template DNA for PCR to obtain a MeJA-SP sequence having a full-length nucleotide sequence of OsMeJA promoter as set forth in SEQ ID NO: 3 and a nucleotide sequence of OsMeJA signal peptide as set forth in SEQ ID NO: 6.

A third primer pair comprising a forward primer having the sequence as set forth in SEQ ID NO: 7 and a reverse primer having the sequence as set forth in SEQ ID NO: 8 was designed, and a PCR was performed using DNA from human embryonic stem cells (Cat. No. PT-5006, purchased from Lonza, Switzerland) as the template DNA for PCR to obtain a nucleotide sequence of hPELN partial human elastin as set forth in SEQ ID NO: 9. This partial human elastin is a partial fragment of a sequence conserved region in a plurality of human elastin with modified mRNA (RNA splicing) with an amino acid sequence as set forth in SEQ ID NO: 25.

A fourth primer pair comprising a forward primer having the sequence as set forth in SEQ ID NO: 10 and a reverse primer having the sequence as set forth in SEQ ID NO: 11 was designed, and a PCR was performed using the rice genomic DNA as the template DNA for PCR to obtain a nucleotide sequence of Ostml rice terminator as set forth in SEQ ID NO: 12.

Figure 1:
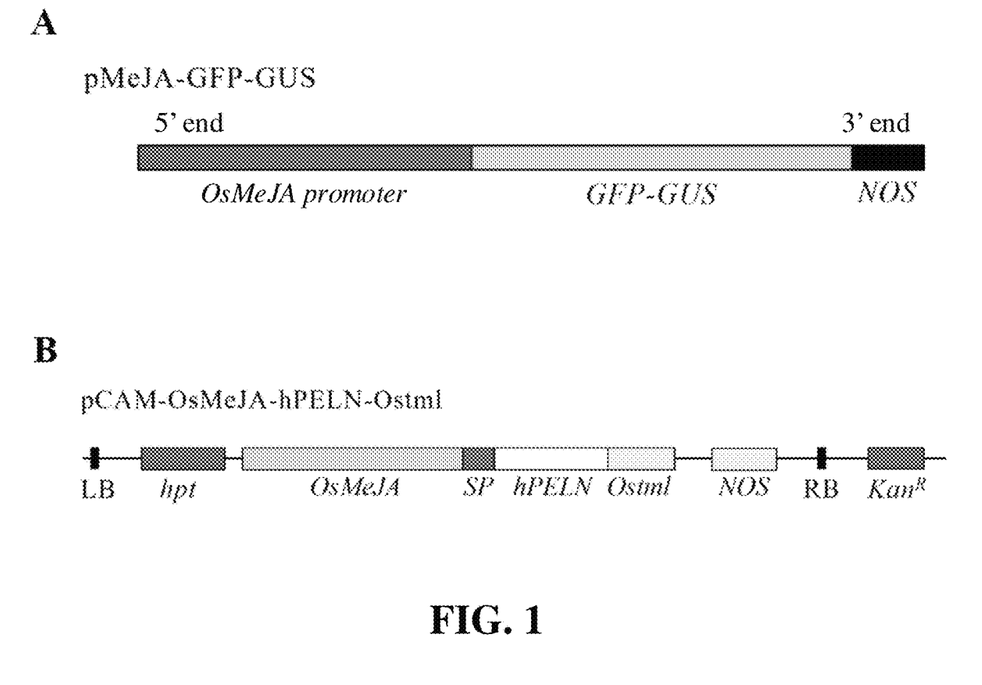

The nucleotide sequences of hPELN partial human elastin and Ostml rice terminator were inserted into the pCAM-BIA1301 vector (binary vector) (purchased from CAMBIA, Australia) using the In-Fusion® HD Cloning Kit (purchased from Takara Bio, Japan) to obtain the pCAM-OsMeJA-hPELN-Ostml plasmid as shown in B of FIG. 1.

Example 3 Analysis of OsMeJA Promoter Activity Via Transient Transfection

Leaves of wild-type tobacco with a leaf age of 30 to 35 days were sterilized and perforated using a perforator to obtain leaf discs with a diameter of 1 centimeter.

The pCAMBIA1390 plasmid (negative control), pCAMBIA1304 plasmid (positive control) and pMeJA-GFP-GUS plasmid were transformed into *Agrobacterium* EHA105. Afterwards, the transformed *Agrobacterium* EHA105 was inoculated into a solid YEP medium containing kanamycin and incubated at 28° ° C. for about 36 hours in the dark to generate a single colony. Positive colonies were picked and incubated separately in MS liquid mediums containing 20 μM acetosyringone to activate the positive *Agrobacterium* EHA105. The concentration ($OD_{600}$) of each positive *Agrobacterium* EHA105 was diluted to 0.8 using an agroinfiltration buffer to obtain an immersion solution. Afterwards, each leaf disk was immersed in each immersion solution and degassed under vacuum for 15 to 20 minutes to completely immerse the leaf discs with the immersion solution so as to obtain the transfected leaf discs.

The transfected leaf discs were removed from the immersion solution and wiped with a hand towel before being placed in a plastic petri dish. An alcohol at a concentration of 0.0095% (control) or an alcohol containing 30 μM methyl jasmonate (MeJA) was sprayed on the surface of each leaf disc, respectively, and then left to stand for 2 days to obtain the transfected leaf discs treated or untreated with MeJA.

Figure 2:
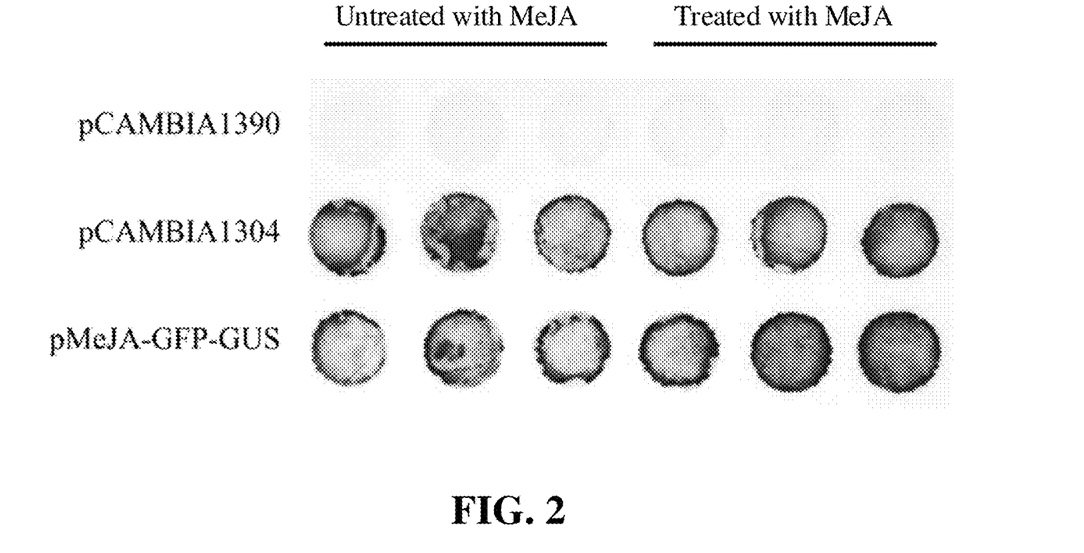
FIG. 2 is a graph showing the GUS staining results of tobacco leaf discs transfected with a pCAMBIA1390 plasmid (negative control), a pCAMBIA1304 plasmid (positive control), and a pMeJA-GFP-GUS plasmid treated or untreated with methyl jasmonate (MeJA).

The transfected leaf discs treated or untreated with MeJA were mixed with 1 ml of X-Gluc solution, respectively, degassed for 60 minutes, and then reacted at 37° C. for 16 hours in the dark. After removing chlorophyll with 95% alcohol, the transfected leaf discs treated or untreated with MeJA were stored in 70% ethanol to obtain each leaf disc stained with GUS. As shown in FIG. 2, the results show that the pMeJA-GFP-GUS-transfected leaf discs treated with MeJA displays a darker blue coloration than the pMeJA-GFP-GUS-transfected leaf discs untreated with MeJA. This indicates that the expression of target proteins can be enhanced in the pMeJA-GFP-GUS-transfected leaf discs treated with MeJA.

Each transfected leaf disc was mixed with 450 μL of GUS extraction buffer and ground at 4° C., centrifuged at 16,000 g and 4° C. The supernatant was removed to obtain each extracted protein. Each extracted proteins was quantified by bovine serum albumin (BSA) standard.

20 μL of each extracted protein was mixed with 30 μL of GUS extraction buffer and 50 μL of GUS analysis buffer, and reacted at 37° C. in the dark for 10 minutes, 40 minutes and 70 minutes to obtain each reaction solution. After reacting for 10 minutes, 40 minutes and 70 minutes, 20 μL of reaction solution and 180 μL of 0.2M $Na_2CO_3$ were mixed to quench the reaction, and the fluorescence value of 4-methylumbelliferone (4-MU) was detected to calculate the relative fluorescence level generated by each extracted protein per unit time.

Figure 3:
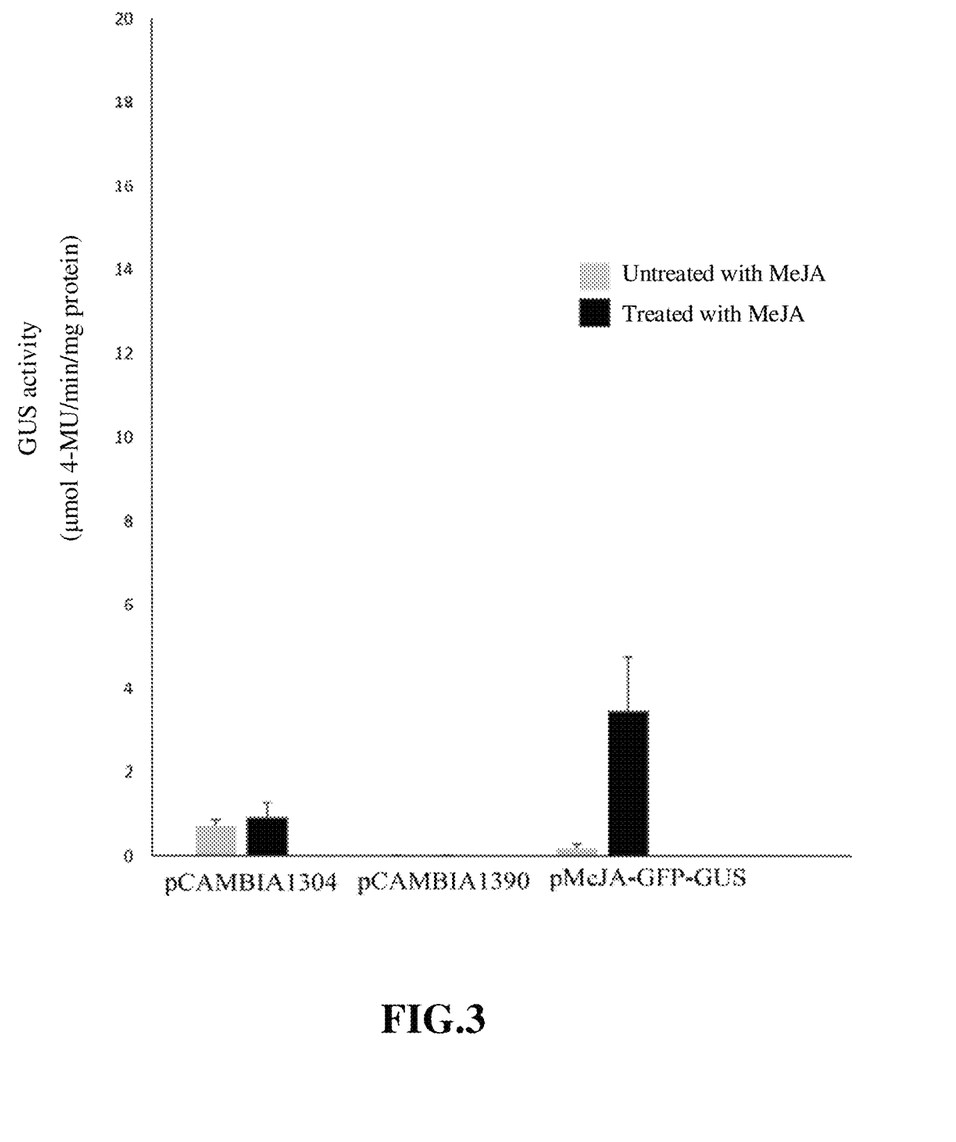
FIG. 3 is a bar graph showing the GUS activity analysis of tobacco leaf discs transfected with a pCAMBIA1390 plasmid (negative control), a pCAMBIA1304 plasmid (positive control), and a pMeJA-GFP-GUS plasmid treated or untreated with methyl jasmonate (MeJA).

The GUS activity of each extracted protein is determined by dividing the relative fluorescence level generated by each extracted protein per unit time by the total protein amount of each extracted protein. 4-MU is a standard that fluoresces upon UV excitation. The GUS activity assay is a relative quantitative method. A fixed amount of total protein extract is reacted with 4-MUG, which will be converted to 4-MU by GUS. The higher the GUS content or the stronger the GUS activity, the more 4-MU is produced. The detected fluorescence intensity per unit of reaction time upon UV excitation is equal to the fluorescence level emitted from the 4-MU standard at a certain concentration, which can be used to represent the activity of GUS protein. The results, as shown in FIG. 3, indicate that the activity of OsMeJA promoter can be enhanced by MeJA treatment.

Example 4 Expression of hPELN Exogenous Protein by OsMeJA Promoter Under Induction of MeJA in Rice Suspension Cells According to Nishimura et al. (2006), the OsMeJA promoter, hPELN and Ostml chimeric genes were introduced into the rice genome through the pCAM-OsMeJA-hPELN-Ostml plasmid to obtain an independently transfected rice strain using an *Agrobacterium* transfection method.

The transfected rice strains were randomly selected, and according to Lu et al. (1998), the rice suspension cells of each transfected rice strain were established and incubated in the dark at 28° C. in a culture medium containing 30 μM MeJA. After incubating for one week, the culture solution of rice suspension cells was collected. The culture solution was centrifuged at 8000 rcf (g) for 20 minutes at 4° C., and the supernatant was removed. The supernatant was filtered using a 5 μm polyvinylidene fluoride membrane (PVDF membrane) to obtain a filtrate. Afterwards, the filtrate was dialyzed against MILLIQ® water (ultrapure water) using a 12 to 14 kD MWCO dialysis membrane, where the volume ratio of the filtrate to MILLIQ® water (ultrapure water) was 1:10, during which MILLIQ® water (ultrapure water) was replaced twice to obtain a dialysate. Finally, the dialysate was filtered with a 0.45 μm PVDF membrane to obtain the rice extract transfected with hPELN.

Figure 4:
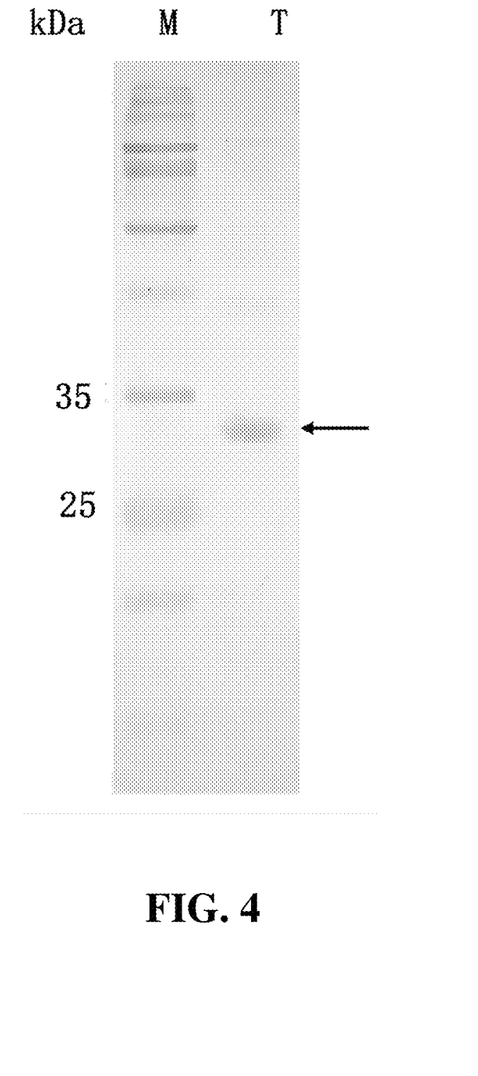
FIG. 4 is a graph showing the Western Blot assay results of anti-human α-elastin of rice extract transfected with hPELN, with an arrow representing about 32 kDa of hPELN exogenous protein.

The rice extract transfected with hPELN was concentrated 10 times, and then a Western blot assay was performed using an anti-human α-elastin antibody (Cat. No.: ab21607, purchased from Abcam, UK). As shown in FIG. 4, the results show that there is about 32 kDa hPELN exogenous protein in the rice extract transfected with hPELN (indicated by the arrow in FIG. 4), confirming that hPELN exogenous protein can be expressed by OsMeJA promoter under induction of MeJA in rice suspension cells and can be secreted from the rice suspension cells into the rice extract.

Figure 5:
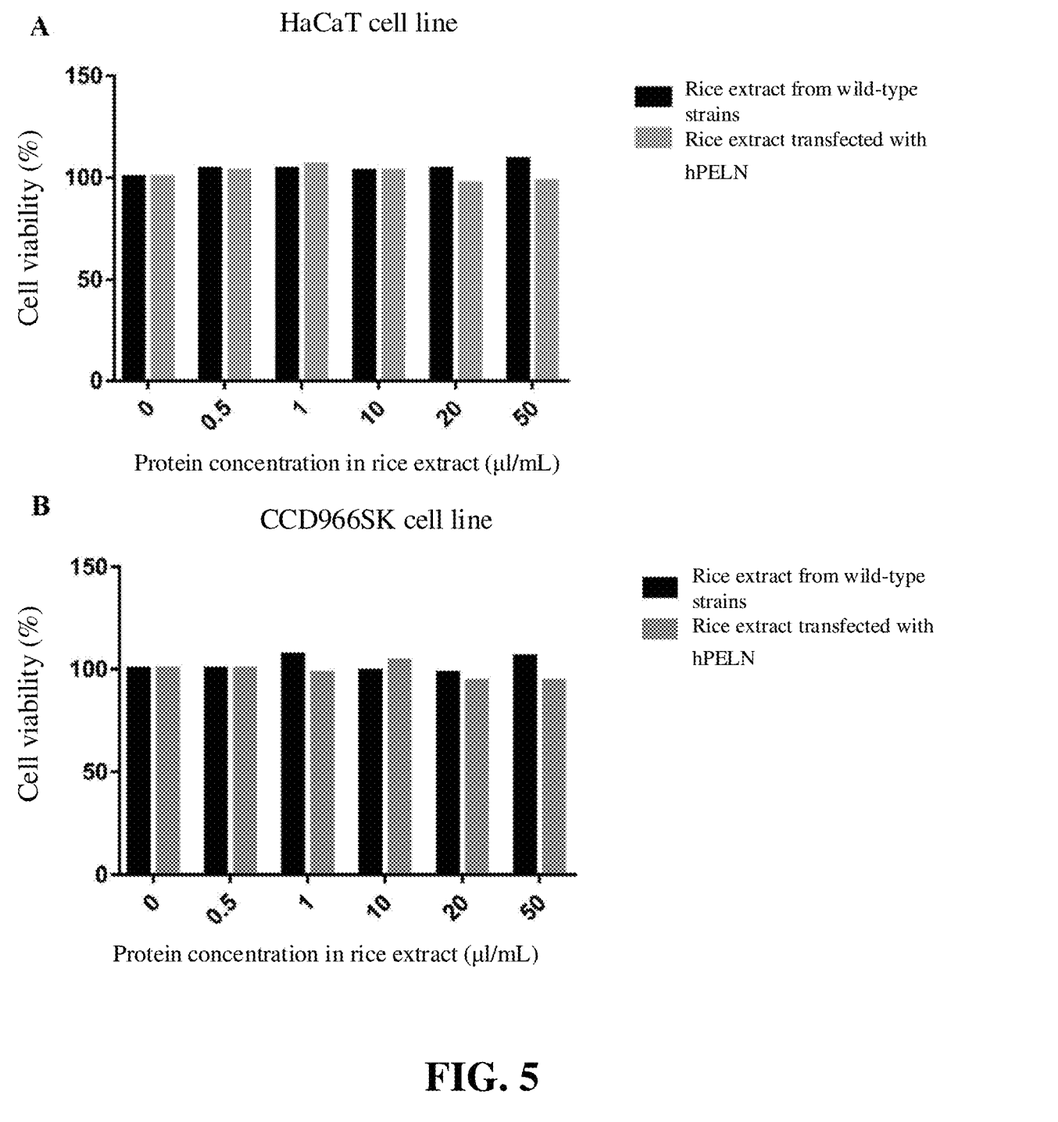
FIG. 5 shows the results of experiments in which a rice extract transfected with hPELN is non-toxic to all cells. In particular, A of FIG. 5 is a bar graph showing the cell viability of HaCaT cell lines after treating the HaCaT cell lines with a rice extract from wild-type strains and a rice extract transfected with hPELN at the protein concentrations of 0.5 µg/mL, 1 µg/mL, 10 µg/mL, 20 µg/mL, and 50 µg/mL. B of FIG. 5 is a bar graph showing the cell viability of CCD966SK cell lines after treating the CCD966SK cell lines with a rice extract from wild-type strains and a rice extract transfected with hPELN at the protein concentrations of 0.5 µg/mL, 1 µg/mL, 10 µg/mL, 20 µg/mL, and 50 µg/mL.

Example 5 Detection of Toxicity of Rice Extract Transfected with hPELN on Human Skin Keratinocytes and Human Epithelial Fibroblasts HaCaT human skin keratinocytes (ATCC® CRL-2404™, purchased from ATCC, USA) were planted in a high-glucose Dulbecco's Modified Eagle Medium (DMEM) containing 5% fetal calf serum and 1% antibiotic P/S in a 96-well plate, and CCD966SK human epithelial fibroblasts (purchased from Bioresource Collection and Research Centre, BCRC, Taiwan, China) were planted in a MEM/EBSS liquid medium containing 0.1 mM non-essential amino acids, 1.5 g/L sodium bicarbonate, 1 mM sodium pyruvate, 10% fetal bovine serum and 1% antibiotic P/S in a 96-well plate at 3,000 to 5,000 cells per well. The 96-well plates were placed and incubated in a cell incubator for 24 hours, so that the cells would be attached to the 96-well plates. Afterwards, the cell culture solution was removed, and 200 μl of cell culture solution containing the rice extract from wild-type strains or the rice extract transfected with hPELN with protein concentrations of 0.5 μg/mL, 1 μg/mL, 10 μg/mL, 20 μg/mL, and 50 μg/mL were added to each well, respectively. The cell culture solution containing the rice extract from wild-type strains or the rice extract transfected with hPELN was incubated for 36 h and then removed. The cells were washed with 1× phosphate buffered saline (PBS). Afterwards, 100 μl of a mixture of cell culture solution and 5 mg/mL of 3-(4,5-dimethylthiazol-2-yl)-2,5-diphenyltetrazolium bromide (MTT) was added to each well, where the volume ratio of MTT to cell culture solution is 1:9. The mixture was incubated in a cell incubator for 3 hours in the dark. After removing the mixture of cell culture solution and MTT, 100 μl of dimethyl sulfoxide (DMSO) was added to each well and shaken in a shaker for 5 minutes. Finally, the absorbance value of $OD_{570}$ was measured to detect the cell viability. The results, as shown in FIG. 5, indicate that both the rice extract from wild-type strains and the rice extract transfected with hPELN with protein concentrations of 0.5 μg/mL, 1 μg/mL, 10 μg/mL, 20 μg/mL, and 50 μg/mL were non-toxic to HaCaT and CCD966SK cell lines.

Example 6 Detection of Effect of Rice Extract Transfected with hPELN on the Expression of Water Retention-Related Genes in CCD966SK Cell Lines The CCD966SK cell lines was plated in a 6-well plate containing cell culture solution at 50,000 cells per well. The 6-well plate was placed and incubated in a cell incubator for 24 hours so that the cells would be attached to the 6-well plate. Afterwards, the cell culture solution was removed, and 200 μl of rice extract from wild-type strains or rice extract transfected with hPELN with a protein concentration of 50 μg/mL were added to each well. After incubating for 36 hours, the culture solution was removed, and the cells were washed with 1× phosphate buffered saline. Afterwards, 0.5 ml of "TRIzol™" reagent (Cat. No. 15596026, Invitrogen) and isopropanone were added to each well to obtain the cell mixture. The cell mixture was allowed to stand at room temperature for 10 minutes and then centrifuged at 12,000×g for 10 minutes at 4° C. Afterwards, the supernatant was removed. The precipitate was washed with 1 ml of 70% alcohol, then centrifuged at 10,000×g for 5 minutes at 4° C. and the supernatant was removed. The precipitate was finally dissolved in diethyl pyrocarbonate-treated water to obtain the RNA of each cell.

cDNA of each cell was prepared using SuperScript™ III Transcriptase (Cat. No. 18080-093) (Thermo Fisher Scientific, Massachusetts, USA). Afterwards, KAPA SYBR® (fluorescent dye) FAST qPCR Kit Master Mix (2X) (Cat. No. KR0389_S, Sigma-Aldrich) was used and a fifth primer pair comprising a forward primer having the sequence as set forth in SEQ ID NO: 13 and a reverse primer having the sequence as set forth in SEQ ID NO: 14, a sixth primer pair comprising a forward primer having the sequence as set forth in SEQ ID NO: 15 and a reverse primer having the sequence as set forth in SEQ ID NO: 16, a seventh primer pair comprising a forward primer having the sequence as set forth in SEQ ID NO: 17 and a reverse primer having the sequence as set forth in SEQ ID NO: 18, and an eighth primer pair comprising a forward primer having the sequence as set forth in SEQ ID NO: 19 and a reverse primer having the sequence as set forth in SEQ ID NO: 20 was designed. A real-time polymerase chain reaction (RT-PCR) was performed using the cDNA of each cell as the template to amplify the nucleotide sequences of human hyaluronan synthase hHAS2 as set forth in SEQ ID NO: 21, human hyaluronan synthase hHAS3 as set forth in SEQ ID NO: 22, human aquaporin hAQP3 as set forth in SEQ ID NO: 23, and human filaggrin hFLG as set forth in SEQ ID NO: 24, respectively.

Figure 6:
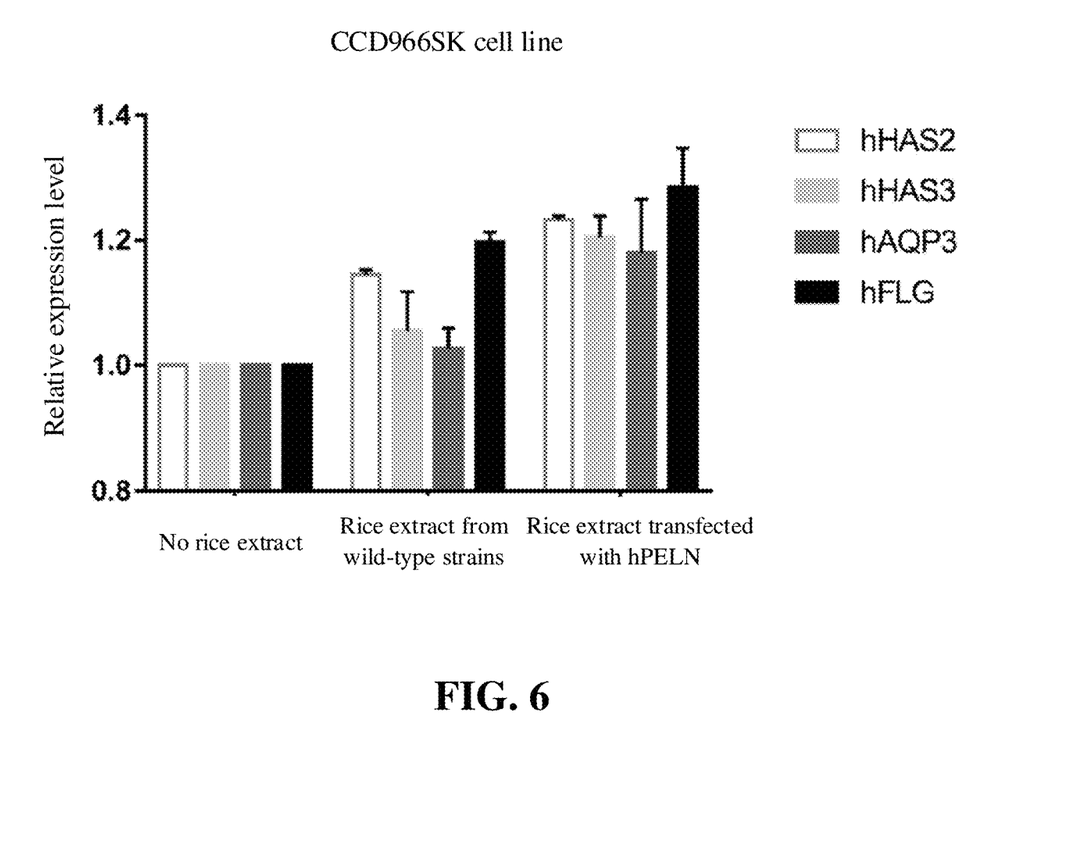
FIG. 6 is a bar graph showing the relative expression levels of water-retaining gene such as human hyaluronan synthase hHAS2 and hHAS3, human aquaporin hAQP3, and human filaggrin hFLG hydroponics genes in the CCD966SK cell lines after treating the CCD966SK cell lines with 200 µl of either a rice extract from wild-type strains or a rice extract transfected with hPELN at a protein concentration of 50 µg/mL.

As shown in FIG. 6, the addition of the rice extract transfected with hPELN to the CCD966SK cell line resulted in 9% and 15% increase in the gene expression levels of human hyaluronan synthases hHAS2 and hHAS3 related to water retention, a 15% increase in the gene expression level of human aquaporin hAQP3 related to cell permeability, and a 9% increase in the gene expression level of human filaggrin hFLG related to cell structure and barrier function in the CCD966SK cell line, as compared to the addition of the rice extract from wide-type strains to the CCD966SK cell line. The increase in the gene expression levels of hHAS2, hHAS3, hAQP3 and hFLG in the cells could enhance the water retention and barrier function in the cells. This suggests that the composition has the function of moisturizing the skin and repairing the skin barrier.

The foregoing examples are merely illustrative of the isolated promoter sequences according to the present disclosure and the use thereof, and are not intended to limit the present disclosure. Any person skilled in the art may make modifications and changes to the above examples without violating the spirit and scope according to the present disclosure. Accordingly, the protection scope according to the present disclosure shall be as set forth in the appended claims.

What is claimed is:

1. A method for enhancing protein expression, comprising following a step of:
   inducing a OsMeJA promoter in an expression cassette or a vector by methyl jasmonate;
   wherein a nucleic acid sequence of the OsMeJA promoter is shown in SEQ ID NO:3.

2. The method according to claim 1, wherein the vector further comprises a transcription initiation sequence, a target gene sequence, a transcription termination sequence and a translation termination sequence.

3. The method according to claim 2, wherein the target gene sequence is a nucleotide sequence of human elastin or a nucleotide sequence of partial human elastin.

4. The method according to claim 3, wherein an amino acid sequence of the partial human elastin is shown as in SEQ ID NO:25.

5. The method according to claim 1, wherein the vector further comprises a restriction site.

6. The method according to claim 1, wherein the vector further comprises a marker gene.

7. The method according to claim 1, wherein the expression cassette further comprises a target gene region.

8. The method according to claim 7, wherein the OsMeJA promoter nucleic acid sequence is located upstream of the target gene region.

9. The method according to claim 1, wherein the expression cassette further comprises a transcription initiation region, a transcription termination region and a translation termination region.

10. The method according to claim 1, wherein the expression cassette comprises, in the nucleic acid sequence, a promoter region, a transcription initiation region, a target gene region, a transcription termination region and a translation termination region; wherein the promoter region consists of the nucleic acid molecule shown in SEQ ID NO: 3.

11. The method according to claim 1, comprising a step of transferring the expression cassette or the vector comprising the nucleic acid molecule shown in SEQ ID NO: 3 into a recipient plant.

12. The method according to claim 11, comprising a step of collecting a cell culture fluid; wherein the cell culture fluid contains a plant or plant cells genetically modified with the nucleic acid molecule shown in SEQ ID NO:3.

* * * * *